United States Patent [19]

Paschke et al.

[11] 4,431,797

[45] Feb. 14, 1984

[54] PREPARATION OF POLY(P-METHYLENEBENZOATE) COPOLYESTERS

[75] Inventors: Edward E. Paschke; John A. Donohue, both of DuPage, Ill.

[73] Assignee: Standard Oil Company (Indiana), Chicago, Ill.

[21] Appl. No.: 445,434

[22] Filed: Nov. 30, 1982

[51] Int. Cl.$^3$ .......................... C08G 63/06; C25B 3/04
[52] U.S. Cl. ........................................ 528/361; 204/75
[58] Field of Search ............................ 204/75; 528/361

[56] References Cited

U.S. PATENT DOCUMENTS

| | | | |
|---|---|---|---|
| 4,130,719 | 12/1978 | Cerefice et al. | 528/361 X |
| 4,182,847 | 1/1980 | Fields et al. | 528/361 |
| 4,220,753 | 9/1980 | Cerefice et al. | 528/361 X |
| 4,381,229 | 4/1983 | Donohue | 204/75 |

*Primary Examiner*—Earl A. Nielsen
*Attorney, Agent, or Firm*—William C. Clarke; William T. McClain; William H. Magidson

[57] ABSTRACT

An electrochemical process is disclosed for the preparation of high molecular weight copolymers of poly(p-methylenebenzoate) and poly(alkyleneterephthalate) wherein ammonia is used in the electrolysis step. The ammonium salts thus formed are removed by heat decomposition. Copolymers are prepared from the resulting electrolysis product.

9 Claims, No Drawings

PREPARATION OF POLY(P-METHYLENEBENZOATE) COPOLYESTERS

FIELD OF THE INVENTION

This invention relates to an improved process for preparation of copolyesters of poly(p-methylenebenzoate) and poly(alkyleneterephthalates), without need for prior isolation procedures wherein the resulting copolymers have an inherent viscosity of at least 0.5 dl/g.

BACKGROUND OF THE INVENTION

Polymerization of p-hydroxymethylbenzoic acid (p-HMBA) affords poly(p-methylenebenzoate), a polymer which exhibits excellent impact properties. The known processes for production of p-hydroxymethylbenzoic acid frequently are cumbersome and run through several stages. For example, p-hydroxymethylbenzoic acid has been prepared by free-radical bromination of p-toluic acid to p-bromomethylbenzoic acid, hydrolysis with aqueous barium hydroxide and subsequent purification by recrystallization from water. Other methods for the preparation of p-hydroxymethylbenzoic acid and/or methyl poly(p-methylenebenzoate) have since been discovered, including:

(a) Hydrolysis of p-toluic acid and derivatives functionalized at the benzylic position, such as p-halomethylbenzoic acid and esters.

(b) Hydrolysis of p-halomethylbenzonitriles, p-hydroxymethylbenzonitrile and p-chloro-toluyl chloride.

(c) Oxidation of p-xylene and substituted p-xylenes, such as p-hydroxymethyltoluene, p-acetoxymethyltoluene and p-xylenediol, and oxidation of p-toluic acid, p-tolualdehyde, and derivatives.

(d) Chloromethylation of benzoic acid and toluene derivatives.

(e) Carboxylation of p-halotoluene compounds via lithium salts.

(f) Disproportionation of terephthaldehyde (Cannizzaro reaction).

(g) Polarographic reduction of dimethyl terephthalate.

(h) Electrochemical reduction of terephthalic acid in aqueous solution.

Of the above methods for preparation of p-hydroxymethylbenzoic acid, the electrolysis of terephthalic acid offers a route to the desired product in one step in good yield and with good selectivity to p-hydroxymethylbenzoic acid.

However, the electrolysis of terephthalic acid requires a catholyte containing a basic solvent diluted suitably to maintain a weak basic condition or an aprotic solvent to which a source of protons has been added. In a suitable method of operation, the catholyte consists of a solvent, preferably water and terephthalic acid with a soluble ammonium salt and ammonia. Reference is made to German Pat. No. 2,642,496 and to commonly-assigned U.S. applications Ser. Nos. 319,120 and 358,222, incorporated herein by reference. The product of electrolysis of terephthalic acid wherein the catholyte contains a soluble ammonium salt and ammonia is the ammonium salt of p-hydroxymethylbenzoic acid which is thereupon acidified. Terephthalic acid and other impurities are typically present in the product.

In more detail, after the electrolysis, German Pat. No. 2,642,496 teaches the electrolysis product can be evaporated to one-half the volume to a concentrate which is then acidified with a mineral acid, especially sulfuric acid, at a temperature of from 5° C. to 15° C., to precipitate the reaction product. The reaction product is washed with water and dried.

Commonly assigned Ser. No. 319,120 teaches that at the end of the electrolysis, the p-hydroxymethylbenzoic acid is isolated from the electrolyte containing ammonium salts by acidifying the catholyte and filtration at a temperature of from 75° C. to 100° C. to remove terephthalic acid. The mother liquor is concentrated under reduced pressure, then cooled to a temperature preferably below 25° C. to obtain p-hydroxymethylbenzoic acid. The impurities in the p-hydroxymethylbenzoic acid obtained by the above typical methods often include terephthalic acid, 4-carboxybenzaldehyde, toluic acid, sulfur, and other oxidized sulfurized by-products if sulfuric acid is used. Other mineral acids, if used, will cause similar impurities. The level of impurities renders the p-hydroxymethylbenzoic acid unusable for polymers having an inherent viscosity of at least 0.50 dl/g without further separate isolation steps.

Commonly assigned Ser. No. 358,222 teaches the crude hydroxymethylbenzoic acid is isolated from the catholyte containing ammonium salts by acidification using known means. The crude p-hydroxymethylbenzoic acid is then hydrogenated to remove 4-carboxybenzaldehyde.

The present invented process differs from the processes taught in commonly-assigned Ser. Nos. 319,120 and 358,222 in that the product of electrolysis of the instant invented process is not acidified to obtain the acids produced by the reduction but instead the ammonium salts, the products of the reduction, are catalytically hydrogenated directly after electrochemical reduction to reduce catalytically 4-carboxybenzaldehyde to the ammonium salt of p-hydroxymethylbenzoic acid. The ammonium salt of p-hydroxymethylbenzoic acid is thereupon decomposed by heat to the free acid.

It is, therefore, an object of this invention to provide a process for the production of poly(p-methylenebenzoate) without need of prior isolation procedures to remove terephthalic acid.

This problem can be solved, surprisingly, by using ammonia or an amine salt in the electrochemical reduction of terephthalic acid to produce an amine salt of p-hydroxymethylbenzoic acid after prior hydrogenation to remove 4-CBA. The amine salt is decomposed in a flash decomposition at a suitable temperature to obtain p-hydroxymethylenebenzoic acid for preparation of poly(p-methylenebenzoate) and of copolyesters of poly(p-methylenebenzoate) and poly(alkyleneterephthalate).

SUMMARY OF THE INVENTION

The present invention relates to a process for the preparation of copolyesters of poly(p-methylenebenzoate) and poly(alkyleneterephthalate) which comprises:

(a) electrochemical reduction of terephthalic acid in an aqueous solution containing terephthalic acid, a weak base and a soluble ammonium salt, (b) hydrogenation to remove 4-carboxybenzaldehyde, (c) removal of water at a temperature of from about 100° C. to about 300° C., (d) polymerization of resultant concentrate by reaction with a glycol in an amount sufficient to prepare a copolyester of poly(p-methylenebenzoate) and poly(alkyleneterephthalate).

DETAILED DESCRIPTION OF THE INVENTION

The present invention provides a process for an electrochemical preparation of p-hydroxymethylbenzoic acid of sufficient purity to prepare copolymers of poly(p-methylenebenzoate) and poly(alkyleneterephthalate). The process requires that the basic solvent in the electrolysis be ammonia or a trialkylamine and that an ammonium salt be used. The process comprises distilling the catholyte after the electrochemical reduction of terephthalic acid, and hydrogenation to remove 4-carboxybenzaldehyde, followed by decomposition of the ammonia and ammonium salt by the application of heat. The p-hydroxymethylbenzoic acid is polymerized in situ by addition of glycol in the presence of a suitable catalyst. Since terephthalic acid is also present to an amount of about 5% to 10%, a resulting polymer can be viewed as substantially a homopolymer or a copolyester of 90% to 95% poly(p-methylenebenzoate) and 5% to 10% poly(alkyleneterephthalate).

Poly(m-methylenebenzoate) homopolymers and copolymers of poly(m-methylenebenzoate) and poly(alkyleneterephthalate) can also be prepared by the instant invented method from isophthalic acid.

Electrochemical methods of preparation of p-hydroxymethylbenzoic acid are taught in German Pat. No. 2,642,496 and commonly-assigned U.S. patent applications Ser. Nos. 319,120 and 358,222 which are incorporated by reference.

In general, the process for the electrochemical preparation of p-hydroxymethylbenzoic acid comprises performing the cathodic reduction in an electrolysis cell having a cathode compartment and an anode compartment. The anode and cathode compartments can be separated by a cation exchange diaphragm, although the presence of a separating diaphragm is not an essential element of the invention. If a separating diaphragm is used, the cathode and anode and the separating diaphragm are preferably in parallel planes. Advantageously, several of the elementary electrolysis cells can be combined in the manner of a filter press.

In general, any metal with a higher hydrogen overvoltage than the potential for the reduction of terephthalic acid to p-hydroxymethylbenzoic acid is suitable for the cathode. Examples of material forming the cathode are lead amalgam, lead and alloys of lead with cadmium, antimony, tin or bismuth.

The anode of the electrolysis cell usually consists of a solid electrically-conducting material which is electrochemically-stable in the anolyte and under the operating conditions considered. Examples of such materials are metals and metalloids such as platinum, platinized titanium, graphite, lead and its alloys, particularly with silver, antimony or tin.

Optionally, any known cation exchange membrane can be used to separate the catholyte from the anolyte, but membranes of the homogeneous type are preferred. These membranes optionally can be reinforced with a screen. For carrying out electrolysis operations over a long period, it is naturally preferred to use membranes which do not swell and which are stable to the action of the various constituents of the catholyte and the anolyte. Examples of such membranes are those of Nafion (trademark of E. I. DuPont de Nemours & Co.) perfluorosulfonic acid.

The catholyte can comprise a neutral solvent, a weakly basic solvent or an aprotic solvent, i.e., acetonitrile, to which a source of protons has been added. Examples of neutral solvents are water, methanol, and other alcohols mixed with water to obtain necessary solvent properties. Examples of basic solvents are ammonia, and trialkylamines such as trimethylamine, triethylamine, etc., which are diluted suitably to maintain a weak basic condition. In a suitable method of operation, the catholyte consists of a solvent, preferably water, and terephthalic acid with a soluble ammonium salt and ammonia. At the start of electrolysis, the catholyte contains sufficient ammonia to form a diammonium salt of terephthalic acid. Less ammonium salt is required as the electrolysis process proceeds. Concentration of ammonia as ammonium hydroxide is within the range of from about 1 gram of ammonium hydroxide per 2 grams of terephthalic acid to about 1 gram of ammonium hydroxide per gram of terephthalic acid and wherein the pH of the resulting solution is at least 6.5, preferably with a pH within the range of from about 8.5 to about 9.5. The concentrations of terephthalic acid and ammonium salt can be either constant when the reaction is carried out continuously, or variable when the reaction is carried out discontinuously. In all cases, the concentration of terephthalic acid is less than the saturation concentration at the temperature of electrolysis; generally, this concentration is greater than 2% by weight, and preferably greater than 3% when the current density is high, these values relating particularly to the constant concentration when the reaction is carried out continuously and to the final concentration when the reaction is carried out discontinuously. The concentration of ammonium salt is usually between about 0.1% to about 10% by weight, and preferably between about 0.1% to about 1.0% by weight, these values relating particularly to the total solution of water, terephthalic acid and other solution components when the reaction is carried out continuously and to the final solution when the reaction is carried out discontinuously. If needed for improved conductivity, ammonium carbonate can be added.

The catholyte can also contain reaction by-products in small amounts, generally less than 1% by weight.

An aqueous acid solution is preferably used as the anolyte, though any other anolyte capable of providing electrical conductivity between the two electrodes can be used. Aqueous solutions of sulphuric or phosphoric acids are usually employed in a concentration generally of 0.1 to 5 mols/liter, and preferably 0.5 to 2 mols/liter. It is preferred that the membrane be sufficiently selective to prevent passage of sulfate or phosphate anions. Alternatively, an amine base or ammonium solution can be employed in equivalent concentrations.

The current density at the cathode is within the range of from about 1 to about 200 amperes per decimeter squared (A/dm$^2$), preferably from about 20 to about 100 A/dm$^2$.

The term "current efficiency" is defined as ratio of consumption in Faradays used to make product to total Faradays used times 100.

The flow of the catholyte in a closed circuit is usually achieved by means of a pump. The circuit can, in addition, contain attached devices such as a heat exchanger or an expansion vessel. The expansion vessel enables terephthalic acid to be added to the catholyte and also some catholyte to be withdrawn in order to extract the p-hydroxymethylbenzoic acid. By-product hydrogen is also removed.

The anolyte can also be circulated, preferably in an anolyte circuit similar to that of the catholyte, so that the pressure on either side of the separating diaphragm can be substantially the same.

At least one spacer is preferably present in the anode and cathode compartment if a cation exchange membrane is used. These spacers serve to prevent deformations of the cation exchange membrane and prevent contact between this membrane and the electrodes. These spacers also help to render uniform the spacing between the membrane and electrodes which contains the electrolyte. These spacers are generally manufactured from synthetic polymers which are chemically inert and which do not conduct electricity; they can be made in the form of interlaced, intertwined, knotted or welded yarns (e.g., woven fabrics, grids or nets) or they can be in the form of plates possessing holes or grooves. In practice, these spacers are oriented along planes which are parallel to those of the electrodes and the separating diaphragm.

Terephthalic acid reduction can be monitored to obtain 100% conversion. Less than 100% conversion is preferable. Less than 96% conversion is more preferable. Increased amounts of impurities such as dihydroxymethylbenzene and toluic acid can result at terephthalic acid conversion levels of greater than 95% to 96%. Percent conversion is preferably balanced to obtain maximum conversion to p-hydroxymethylbenzoic acid and minimum conversion to undesirable by-products.

Terephthalic acid, under ambient conditions being virtually insoluble in water, requires a weak base as a reactant to form a soluble salt in water. Examples of weak bases are ammonia, trimethylamine and triethylamine, but ammonia is preferably used.

In the practice of the electrolysis step a weak base, i.e., ammonia, and a salt such as an ammonium salt are added initially to the catholyte, the ammonia in a concentration sufficient to dissolve the terephthalic acid in the solvent, i.e., water, aqueous ammonia, etc. but which is preferably water, and an ammonium salt to carry the current. After an initial period of operation, a monoammonium salt of terephthalic acid is added to maintain a basic condition sufficient to cause additions of terephthalic acid to dissolve, with pH above 6.5 and preferably with a pH within the range of about 8.5 to about 9.5, to insure complete solubility of the terephthalic acid.

In the purification of the crude p- and m-hydroxymethylbenzoic acid, the first step is hydrogenation of the 4- and 3-carboxybenzaldehyde to p- and m-hydroxymethylbenzoic acid (p- and m-HMBA). Any suitable catalyst, such as platinum or palladium, can be used. Noble metal catalysts, such as platinum on carbon, are preferred. Typical hydrogenation processes are taught in U.S. Pat. No. 3,726,915; German Offen. No. 2,045,747; Japanese Kokai Tokkyo Koho No. 80,143,933; Belgium Pat. No. 876,860; German Offen. No. 2,709,525 and U.S. Pat. No. 4,260,817.

Accordingly, at the end of electrolysis of terephthalic acid the catholyte containing ammonium p-hydroxymethylenebenzoate is catalytically hydrogenated to remove 4-carboxybenzaldehyde (4-CBA) and is distilled or dried to remove the water.

Distillation is preferably under pressure of from 50 to 500 psi and at a temperature of from 60° C. to 90° C. to reduce possible product decomposition. After water has been removed from the catholyte solution, the temperature is raised to within the range of from about 150° C. to about 190° C. wherein the ammonium salts of p-hydroxymethylbenzoic acid and terephthalic acid formed during the process of electrolysis decompose to free ammonia or the amine and the respective acids or esters.

Any suitable means of removing the water content of the electrolyte and decomposing the ammonium salts can be used. As noted heretofore, a distillation column can be used to remove the water which is followed by use of a drying operation. Alternate methods of removing the water and decomposing the ammonium salts include use of drying equipment such as a spray dryer, a drum dryer, a fluidized bed dryer and similar equipment. The catholyte solution is injected into a spray dryer at a dryer temperature of from about 150° C. to 190° C. The flash evaporation in the spray dryer prevents product decomposition and the temperature causes the ammonium salts to decompose. The alternative use of a drum dryer requires the dryer drum be enclosed to recover the ammonia generated by the decomposed ammonium salts.

The recovered dryer product of acids, esters and ammonium salts remaining after flash evaporation contains terephthalic acid of from about 5% to about 10% of the p-hydroxymethylbenzoic acid present. The recovered acids, esters and recovered salts are reacted with a glycol in presence of a catalyst to prepare a copolyester of poly(p-methylenebenzoate) and poly(alkyleneterephthalate).

In general, polymerization conditions and ranges for preparing copolyesters of from p- and m-hydroxymethylbenzoic acid (p-HMBA and m-HMBA) containing dicarboxylic acid impurities are the same as when using highly purified p-HMBA and m-HMBA.

p-HMBA and m-HMBA can be polymerized in a conventional catalytic polymerization. A variety of organotin, titanium, and other metal catalysts known in the art can be employed. The catalyst preferably is added at the start of the first stage. During the first stage, p-HMBA is heated above its melting point (184° C.) up to 265° C. at atmospheric pressure under an inert atmosphere for approximately 110 minutes. Water is removed via distillation. The reaction can be run at increased pressure or at sub-atmospheric pressure.

The glycol preferably is added during the first stage of the polymerization. The glycol has the general structure:

HO—R'—OH where R' is $(CH_2)_n$ with $n=2-20$, R' is cycloaliphatic or R' is aliphatic aryl. Examples are ethylene glycol, cyclohexanedimethanol and p-benzenedimethanol. The preferred glycol is ethylene glycol. A molar excess of glycol to dicarboxylic acid impurity is added in the range of 1.1 to 5.01 (preferably 1.51) since the excess glycol will be removed during the polycondensation stage. The excess glycol compensates for any loss of glycol due to volatility prior to incorporation into the polymer structure.

In general, the polymerization reaction is carried out with a monomer catalyst mixture wherein the ratio of catalyst to monomer is 1.0 to 0.001% by weight. Typical catalysts which can be used are tetrabutyl titanate, tetraisopropyl titanate, dibutyl tin maleate, tin butyl stannoic anhydride and dihydroxy tin chloride. A preferred catalyst is butyl stannoic anhydride because of activity.

The pressure at which the process is operated is not critical and it has been found convenient to conduct at least part of the process at atmospheric. However, since the reaction results in the production of volatile condensation products, it has been found advantageous to complete the reaction under reduced pressure to assist the removal of such volatile materials.

The reaction is preferably effected in the absence of air which can cause some degradation and undesirable coloring of the products, and, if desired, can be effected under a constant flow of an inert gas, that is, a gas which does not interfere with polymerization reaction, for example, nitrogen which can conveniently be passed through the reaction mixture to stir the mixture and aid the removal of the volatile reaction products.

The reaction is conveniently effected in two stages, the first stage being to drive off any initial volatile condensation products and to obtain a homogeneous melt, and the second stage, at a higher temperature than the first stage, to continue the polymerization to a desired degree of conversion.

Reactions are run at a temperature of from 100° C. to 300° C. under an inert gas as a sweep for a period of from 0.5 to 10 hours. Preferred conditions are 150° C. to 200° C. for 120 minutes under a nitrogen sweep gas. Partial vacuum of 600 to 100 mm Hg is then applied for a period of 0.1 to 10 hours, preferred 0.25 to 4 hours, and full vacuum, 5.0 to 0.01 mm Hg, applied for 1 to 8 hours with the temperature maintained at 250° C. to 310° C. The product, which is a melt, is removed from the reactor, cooled to a solid state under 100° C. and finely ground to about 20 to 40 mesh. The material can then be solid state polymerized by heating at about 150° C. to 250° C. at 50 to 0.1 mm Hg vacuum for 6 to 24 hours. Preferred conditions are 220° C. to 240° C. at 0.5 mm Hg for 8 to 16 hours. Inherent viscosity (I.V.) is measured in deciliters/gram (dl/g) in a 60/40 phenol/tetrachloroethane solvent at 30° C.

The process of the instant invention possesses numerous advantages. The process eliminates the necessity of eliminating the contaminant terephthalic acid or acidifying the catholyte solution with a mineral acid, usually sulfuric acid, which in turn introduces sulfur contamination into the desired product. Further purification to remove the sulfur is thereupon necessary. The ammonia is recovered for recycle into the process. The process can be operated upon either a batch or continuous basis, with the advantages inherent in each method.

In order to facilitate a clear understanding of the invention, i.e., the process for preparing copolymers of p- and m-hydroxymethylbenzoic acid containing dicarboxylic acid impurities, the following specific embodiments are described in detail. It should be understood, however, that the detailed expositions of the process, while indicating preferred embodiments, are given by way of illustration only since various changes and modifications within the spirit and scope of the invention will become apparent to those skilled in the art from this detailed description.

The following examples illustrate the invention. The chemical yields indicated are yields of p-hydroxymethylbenzoic acid relative to quantities of terephthalic acid present. Concentrations of solutions are expressed as the number of grams of solute per liter of solution.

EXAMPLE I

Reduction of terephthalic acid to p-hydroxymethylbenzoic acid was carried out in an electrolysis cell in the following manner. The cathode was electrically pure lead amalgamated with 99.9% pure mercury. The membrane was of sulfonated fluorocarbon polymer. In construction the two-compartment electrolysis cell comprised an inlet plate of polyvinylchloride (PVC) which was fitted to a second plate of the same size of lead amalgam which constituted the cathode. PVC inserts between the cathode plate and the semi-permeable membrane acted as spacers to separate the cathode and membrane sufficiently to permit catholyte flow. The anode was an electrically pure ½-inch titanium plate coated with platinum to a thickness of 250 micro-inches. Anode and membrane were separated by PVC spacers to permit the anolyte to flow through the cell. An external reservoir for the anolyte served as an oxygen gas separator. An external reservoir for the catholyte served as a hydrogen gas separator. In operation, electrolyte was continuously pumped from the reservoir to the electrolysis cell and returned to the reservoir through a heat exchanger. Periodic additions of mercuric acetate (Hg(Ac)$_2$) were made each ½ hour to the electrolysis cell during the course of the run. Intermittent operation for 13¾ hours was over a period of 3 days.

Current density was controlled so as to maintain consumption of electricity slightly below the calculated quantity of 4 Faradays required for one equivalent weight of terephthalic acid converted.

An aqueous solution of 2% sulfuric acid, approximately 0.2 mols/liter of water, was used as the anolyte. The catholyte consisted of water, terephthalic acid, ammonia and a soluble ammonium salt, ammonium carbonate (NH$_4$)$_2$CO$_3$. Terephthalic acid was added during electrolysis to maintain the reduction rate. Analyses of the catholyte were made periodically by liquid chromatography and calculated as mg/ml of electrolyte solution. Liquid chromatographic analyses were as the free acids but products of electrochemical reduction existed in the catholyte as ammonium salts prior to analysis.

Table I

| Electrochemical Reduction of Terephthalic Acid-(NH$_4$)$_2$CO$_3$ Electrolyte Lead Amalgam Cathode | |
|---|---|
| Run No. (5995) | 110 |
| Conditions | |
| (NH$_4$)$_2$CO$_3$-g Added | 200 |
| Terephthalic Acid (TA) g Added During Run | 2455 |
| Ammonium Hydroxide -(29% Solution)-ml Added During Run | 1251 |
| Water-ml | 4800 |
| Current Density-A/dm$^2$(max.) | 75 |
| Faradays/mole TA | 4.8 |
| Actual Run Time-Hours | 13¾ |
| Results | |
| TA Conversion (wt) % | 92 |
| p-HMBA Yield (wt) % of TA Converted | 87 |
| Current Efficiency % | 72 |
| Catholyte Analysis End of Run mg/ml | |
| p-HMBA | 181 |
| Terephthalic Acid | 12 |
| 4-Carboxybenzaldehyde | 2.5 |
| Toluic Acid | 0.8 |

EXAMPLE II

This example illustrates the polymerization by the invented process of an electrolytic solution of p-hydroxymethylbenzoic acid containing dicarboxylic acid impurities. An ammonium solution (530.3 ml) of p-hydroxymethylbenzoic acid ammonium salt with a pH of 10.5 and with a concentration of 0.33 g/ml, containing impurity levels of 0.54 (wt) percent terephthalic acid, 0.051 (wt) percent 4-carboxybenzaldehyde, and 0.01 (wt) percent p-toluic acid was placed in a one-liter reactor equipped with a nitrogen sweep, stirrer, distillation column and a vacuum side-arm. To the solution was added 0.66 g of ethylene glycol and 0.10 g of butyl stannoic anhydride catalyst. The solution was heated at 107° C. to 250° C. for 172 minutes at atmospheric pressure to remove water and ammonia. The pressure was reduced to 1.25 mm Hg and the temperature was increased to 265° C. over the following 27 minutes. Polycondensation was continued at 265° C. for 170 minutes at 0.32–1.20 mm Hg vacuum level. The polymer had a 0.58 dl/g inherent viscosity. Nitrogen analysis of the polymer showed only 0.147 percent of nitrogen which confirms the polyester composition as the principal component.

EXAMPLE III

Example II was essentially repeated except without adding any ethylene glycol to the polymerization. The polymer had only a 0.46 dl/g inherent viscosity.

What is claimed is:

1. An electrochemical process for preparation of polymers of p-hydroxymethylbenzoic acid which process comprises:
   (a) electrochemical reduction in aqueous solution of terephthalic acid to ammonium salt of p-hydroxymethylbenzoic acid,
   (b) hydrogenation of said aqueous solution to remove 4-carboxybenzaldehyde,
   (c) removal of water content of said aqueous solution,
   (d) decomposition of said ammonium salt of p-hydroxymethylbenzoic acid to p-hydroxymethylbenzoic acid at a temperature within the range of from about 150° C. to about 190° C.,
   (e) polymerization of said p-hydroxymethylbenzoic acid monomer under polymerization conditions in presence of a glycol and a suitable catalyst wherein resulting polymer has an inherent viscosity of at least 0.5 dl/g.

2. The process of claim 1 wherein said glycol is of the structure HO—R'—OH wherein R' is selected from the group consisting of —$(CH_2)_n$— wherein n is a whole number of from 2 to 20, a cycloaliphatic moiety containing 5 to 20 carbon atoms and an aliphatic aryl moiety of from 7 to 20 carbon atoms.

3. The process of claim 2 wherein molar ratio of said glycol to said p-hydroxymethylbenzoic acid is in the range of from about 1:1 to 5.0:1.

4. The process of claim 3 wherein said molar ratio is 1.5:1.

5. The process of claim 2 wherein said glycol is ethylene glycol.

6. The process of claim 2 wherein said glycol is p-benzenedimethanol.

7. The process of claim 1 wherein said catalyst is selected from the group consisting of tetrabutyl titanate, tetraisopropyl titanate, dibutyl tin maleate, tin butyl stannoic anhydride and dihydroxy tin chloride.

8. The process of claim 1 wherein said catalyst is butyl stannoic anhydride.

9. The process of claim 1 wherein ratio of said catalyst to said monomer is 1.0 to 0.001% by weight.

* * * * *

UNITED STATES PATENT OFFICE
CERTIFICATE OF CORRECTION

Patent No. 4,431,797　　　　　　　　　Dated February 14, 1984

Inventor(s) Edward E. Paschke and John A. Donohue

It is certified that error appears in the above-identified patent and that said Letters Patent are hereby corrected as shown below:

Patent reads, col. 6, line 59:

"5.01 (preferably 1.51)" and should read

--5.0/1 (preferably 1.5/1)--.

Signed and Sealed this

Fourteenth Day of August 1984

[SEAL]

Attest:

GERALD J. MOSSINGHOFF

Attesting Officer　　　Commissioner of Patents and Trademarks